United States Patent
Melvin

(10) Patent No.: US 7,850,729 B2
(45) Date of Patent: Dec. 14, 2010

(54) DEFORMING JACKET FOR A HEART ACTUATION DEVICE

(75) Inventor: David Boyd Melvin, Loveland, OH (US)

(73) Assignee: The University of Cincinnati, Cincinnati, OH (US)

( * ) Notice: Subject to any disclaimer, the term of this patent is extended or adjusted under 35 U.S.C. 154(b) by 1219 days.

(21) Appl. No.: 11/298,428

(22) Filed: Dec. 8, 2005

(65) Prior Publication Data

US 2006/0187550 A1 Aug. 24, 2006

Related U.S. Application Data

(63) Continuation of application No. PCT/US2004/018298, filed on Jun. 9, 2004, and a continuation-in-part of application No. 10/667,877, filed on Sep. 22, 2003, now abandoned, and a continuation-in-part of application No. 10/197,973, filed on Jul. 18, 2002, now abandoned.

(60) Provisional application No. 60/477,086, filed on Jun. 9, 2003.

(51) Int. Cl.
*A61M 1/12* (2006.01)
(52) U.S. Cl. .................................. 623/3.16; 600/17
(58) Field of Classification Search ............. 623/3.26, 623/3.29, 3.1, 3.16, 3.12; 600/16, 17
See application file for complete search history.

(56) References Cited

U.S. PATENT DOCUMENTS 2,826,193 A * 3/1958 Vineberg ............... 601/153
3,053,249 A 9/1962 Smith
3,176,316 A 4/1965 Bodell
3,455,298 A 7/1969 Anstadt (Continued)

FOREIGN PATENT DOCUMENTS

EP 0119357 3/1987

(Continued)

OTHER PUBLICATIONS

Melvin, D.V.; Conkle, D; Roberts, A; Stinson, E; "Cardiac Perforamnce and Myocardial Contractility After Experimental Mechanical Ventricular Assistance", J. Thoracic and Cardiovascular Surgery vol. 65, Nol. 6, Jun. 1973. (pp. 876-881).

(Continued)

*Primary Examiner*—George R Evanisko
(74) *Attorney, Agent, or Firm*—Wood, Herron & Evans, LLP

(57) ABSTRACT

The invention consists of a cushioned active cyclically deforming cushion or jacket (39) that surrounds the outer or epicardial surface of at least one chamber (2, 3, 4, 5) of the natural heart, including its base, configured so that internal components may be suspended from the jacket (39) by heart wall-penetrating cords to complete a restraining harness over the entire 3-dimensional boundary of the chamber or chambers. The cushion or jacket (39) provides protective and stabilizing openings (8, 9, 10) for atria and their inflow valves as well as for great vessels and their outflow valves. It is equipped with one or more actuator mechanisms (37, 38) that cyclically change shape at one or more sites, thus altering heart wall shape and chamber volume.

20 Claims, 10 Drawing Sheets

U.S. PATENT DOCUMENTS

| | | | |
|---|---|---|---|
| 3,513,836 A | 5/1970 | Sausse | |
| 3,590,815 A | 7/1971 | Schiff | |
| 3,613,672 A | 10/1971 | Schiff | |
| 3,668,708 A | 6/1972 | Tindal | |
| 3,713,439 A | 1/1973 | Cabazudo et al. | |
| 3,791,388 A | 2/1974 | Rosen et al. | |
| 3,827,426 A | 8/1974 | Page et al. | |
| 3,835,864 A | 9/1974 | Rasor et al. | |
| 3,983,863 A | 10/1976 | Janke et al. | |
| 4,127,109 A * | 11/1978 | Fourney et al. | 128/899 |
| 4,149,277 A | 4/1979 | Bokros | |
| 4,187,558 A | 2/1980 | Dahlen et al. | |
| 4,192,293 A | 3/1980 | Asrican | |
| 4,255,820 A | 3/1981 | Rothermel et al. | |
| 4,453,537 A | 6/1984 | Spitzer | |
| 4,519,392 A | 5/1985 | Lingua | |
| 4,536,893 A | 8/1985 | Parravicini | |
| 4,585,458 A | 4/1986 | Kurland | |
| 4,597,766 A | 7/1986 | Hilal et al. | |
| 4,621,617 A | 11/1986 | Sharma | |
| 4,690,134 A | 9/1987 | Snyders | |
| 4,713,075 A | 12/1987 | Kurland | |
| 4,773,910 A | 9/1988 | Chen et al. | |
| 4,809,676 A | 3/1989 | Freeman | |
| 4,846,831 A | 7/1989 | Skillin | |
| 4,904,255 A | 2/1990 | Chareire et al. | |
| 4,917,700 A | 4/1990 | Aikins | |
| 4,936,857 A | 6/1990 | Kulik | |
| 4,946,377 A | 8/1990 | Kovach | |
| 4,957,477 A | 9/1990 | Lundback | |
| 4,964,414 A | 10/1990 | Handa et al. | |
| 5,049,155 A | 9/1991 | Bruchman et al. | |
| 5,061,283 A | 10/1991 | Silvestrini | |
| 5,109,843 A | 5/1992 | Melvin et al. | |
| 5,116,372 A | 5/1992 | Laboureau | |
| 5,119,804 A | 6/1992 | Anstadt | |
| 5,131,905 A | 7/1992 | Grooters | |
| 5,139,517 A | 8/1992 | Corral | |
| 5,169,381 A | 12/1992 | Snyders | |
| 5,192,314 A | 3/1993 | Daskalakis | |
| 5,197,983 A | 3/1993 | Berman et al. | |
| 5,201,880 A | 4/1993 | Wright et al. | |
| 5,217,495 A | 6/1993 | Kaplan et al. | |
| 5,256,132 A | 10/1993 | Snyders | |
| 5,258,021 A | 11/1993 | Duran | |
| 5,334,217 A | 8/1994 | Das | |
| 5,345,949 A | 9/1994 | Shlain | |
| 5,358,519 A | 10/1994 | Grandjean | |
| 5,370,685 A | 12/1994 | Stevens | |
| 5,383,840 A | 1/1995 | Heilman et al. | |
| 5,385,528 A | 1/1995 | Wilk | |
| 5,443,504 A | 8/1995 | Hill | |
| 5,456,715 A | 10/1995 | Liotta | |
| 5,484,391 A | 1/1996 | Buckman et al. | |
| 5,487,760 A | 1/1996 | Villafana | |
| 5,533,958 A | 7/1996 | Wilk | |
| 5,558,617 A | 9/1996 | Heilman et al. | |
| 5,571,176 A | 11/1996 | Taheri | |
| 5,581,176 A | 12/1996 | Lee | |
| 5,593,424 A | 1/1997 | Northrup, III | |
| 5,643,308 A | 7/1997 | Markman | |
| 5,655,548 A | 8/1997 | Nelson et al. | |
| 5,667,526 A | 9/1997 | Levin | |
| 5,697,978 A | 12/1997 | Sgro | |
| 5,702,343 A | 12/1997 | Alferness | |
| 5,709,695 A | 1/1998 | Northrup | |
| 5,713,954 A | 2/1998 | Rosenberg et al. | |
| 5,727,569 A | 3/1998 | Benetti et al. | |
| 5,738,626 A | 4/1998 | Jarvik | |
| 5,738,627 A | 4/1998 | Kovacs et al. | |
| 5,749,883 A | 5/1998 | Halpern | |
| 5,800,528 A | 9/1998 | Lederman et al. | |
| 5,824,071 A | 10/1998 | Nelson et al. | |
| 5,910,124 A | 6/1999 | Rubin | |
| 5,957,977 A * | 9/1999 | Melvin | 623/3.1 |
| 5,961,440 A | 10/1999 | Schweich et al. | |
| 5,981,827 A | 11/1999 | Devlin et al. | |
| 6,019,722 A | 2/2000 | Spence et al. | |
| 6,045,497 A | 4/2000 | Schweich et al. | |
| 6,050,936 A | 4/2000 | Schweich et al. | |
| 6,059,715 A | 5/2000 | Schweich et al. | |
| 6,077,214 A | 6/2000 | Mortier et al. | |
| 6,085,754 A | 7/2000 | Alferness et al. | |
| 6,110,100 A | 8/2000 | Talpade | |
| 6,123,662 A | 9/2000 | Alferness et al. | |
| 6,125,852 A | 10/2000 | Stevens et al. | |
| 6,162,168 A | 12/2000 | Schweich et al. | |
| 6,165,119 A | 12/2000 | Schweich et al. | |
| 6,165,120 A | 12/2000 | Schweich et al. | |
| 6,179,791 B1 | 1/2001 | Krueger | |
| 6,183,411 B1 * | 2/2001 | Mortier et al. | 600/16 |
| 6,214,047 B1 | 4/2001 | Melvin | |
| 6,221,103 B1 | 4/2001 | Melvin | |
| 6,260,552 B1 | 7/2001 | Mortier et al. | |
| 6,261,222 B1 | 7/2001 | Schweich, Jr. et al. | |
| 6,264,602 B1 | 7/2001 | Mortier et al. | |
| 6,293,906 B1 | 9/2001 | Vanden Hoek et al. | |
| 6,319,231 B1 | 11/2001 | Andrulitis | |
| 6,324,430 B1 | 11/2001 | Zarinetchi et al. | |
| 6,324,431 B1 | 11/2001 | Zarinetchi et al. | |
| 6,332,863 B1 | 12/2001 | Schweich, Jr. et al. | |
| 6,332,864 B1 | 12/2001 | Schweich, Jr. et al. | |
| 6,332,893 B1 | 12/2001 | Mortier et al. | |
| 6,375,611 B1 | 4/2002 | Voss et al. | |
| 6,402,680 B2 | 6/2002 | Mortier et al. | |
| 6,409,760 B1 | 6/2002 | Melvin | |
| 6,425,856 B1 | 7/2002 | Shapland et al. | |
| 6,579,226 B2 | 6/2003 | Vanden Hoek et al. | |
| 6,582,375 B2 | 6/2003 | Melvin et al. | |
| 6,592,619 B2 | 7/2003 | Melvin | |
| 6,620,095 B2 | 9/2003 | Taheri | |
| 6,733,510 B1 | 5/2004 | Melvin | |
| 6,764,510 B2 | 7/2004 | Vidlund et al. | |
| 6,887,192 B1 * | 5/2005 | Whayne et al. | 600/16 |
| 6,988,982 B2 | 1/2006 | Melvin et al. | |
| 7,118,525 B2 | 10/2006 | Coleman et al. | |
| 7,361,191 B2 | 4/2008 | Melvin | |
| 2003/0023132 A1 | 1/2003 | Melvin et al. | |
| 2004/0059180 A1 | 3/2004 | Melvin | |
| 2005/0197527 A1 | 9/2005 | Bolling | |
| 2005/0250976 A1 | 11/2005 | Melvin | |
| 2006/0155159 A1 | 7/2006 | Melvin | |
| 2006/0178551 A1 | 8/2006 | Melvin | |
| 2006/0187550 A1 | 8/2006 | Melvin | |
| 2006/0189840 A1 | 8/2006 | Walsh et al. | |
| 2008/0081942 A1 | 4/2008 | Pai et al. | |

FOREIGN PATENT DOCUMENTS

| | | |
|---|---|---|
| EP | 0583012 | 7/1996 |
| SU | 1191076 A | 11/1985 |
| WO | WO9829041 | 7/1998 |
| WO | WO9930647 | 6/1999 |
| WO | WO9953977 | 10/1999 |
| WO | WO0002500 | 1/2000 |
| WO | WO0006026 | 2/2000 |
| WO | WO0006027 | 2/2000 |
| WO | WO0006028 | 2/2000 |
| WO | WO0016700 | 3/2000 |
| WO | WO0018320 | 4/2000 |
| WO | WO0047270 | 8/2000 |
| WO | WO0167985 | 2/2001 |
| WO | WO0128455 | 4/2001 |
| WO | WO0185061 | 11/2001 |

| WO | WO0191667 | 12/2001 |
| WO | WO0195830 | 12/2001 |
| WO | WO0195831 | 12/2001 |
| WO | WO0195832 | 12/2001 |

OTHER PUBLICATIONS

Melvin, D.B., "Cardiovascular Surgery: Myocardial Preservation, Cardiorespiratory Support I", American Heart Assoc. Abstract, Circulation Part II, vol. 68, No. 4; Scientific Sessions for Nurses; 37th Ann. Meeting; Nov. 14-17, 1983. (1 Page).

Melvin, D.; Schima, H.; Losert, U.; Wolner, E., "Long-Term Ventricular Wall Actuation: Can and Should it be Systematically Explored?", Artificial Organs, vol. 20, No. 1, 1996. (pp. 63-68).

Melvin, D.B., et al., "A Physical Analog of the Failing Left Ventricle for In Vitro Studies of Mechanical Wall Actuation", Artificial Organs, vol. 20, No. 3, 1996. (pp. 227-239).

Melvin, D.B., et al., "Reduction of Ventricular Wall Tensile Stress by Geometric Remodeling Device", ASAIO Journal (Abstract), vol. 45, No. 2 p. 166, Mar. 17, 1999. (1 page).

Melvin, D.B., "Device-Induced Ventricular Geometric Remodeling: Appraisal of Critical Issues", J. of Cardiac Surgery (Accepted for publication), Presented at the 3rd Symposium of the Soc. of Cardiac Volume Reduction, Apr. 9, 2000 in Osaka, Japan.

Four-page International Search Report for PCT/US2003/030302, mailed Mar. 24, 2004.

Two-page International Search Report for PCT/US2004/018277, mailed Nov. 2, 2004.

Four-page International Search Report for PCT/US2004/018277, mailed Nov. 19, 2004.

One-page International Search Report for US/PCT2003/025986, mailed Feb. 3, 2004.

Farrar, et al. (1992), "A New Skeletal Linear-pull Energy Convertor as a Power Source for Prosthetic Circulatory Support Devices", Journal of Heart and Lung Transplantation, pp. S341-S349.

Farrar, et al. (1995), "Mechanical Advantage of Skeletal Muscle as a Cardiac Assist Power Sources", ASAIO Journal, pp. M481-M484.

Sasaki, et al. (1992), "A Skeletal Muscle Actuator for an Artificial Heart", ASAIO Journal, pp. M507-M511.

Acker, et al. (1987), "Skeletal Muscle as the Potential Power Source for a Cardiovascular Pump; Assessment in Vivo Science", Science, vol. 236, pp. 324-327.

Salmons, et al. (1992), "Cardiac Assistance From Skeletal Muscle: A Critical Appraisal of the Various Approaches", British Heart Journal, vol. 68, pp. 333-338.

Ugolini (1986), "Skeletal Muscle for Artificial Heart Drive: Theory and in Vivo Experiments", Biomechanical Cardiac Assist, pp. 193-211.

Reichenbach, et al. (1997), "In Vivo Studies of an Implantable Energy Convertor for Skeletal Muscle Powered Cardiac Assist", ASAIO Journal, vol. 43, pp. M668-M672 (and Abstract).

Geddes, et al. (1991), "Power Capability of Skeletal Muscle to Pump Blood", Trans Am Soc. Artif. Intern Organs, vol. XXXVII, pp. 19-23.

Reichenbach, et al. (1992), "Characterization and Work Optimization of Skeletal Muscle as a VAD Power Source", ASAIO Journal, pp. M359-M363.

Melvin, et al. (1997), "Coupling of Skeletal Muscle to a Prosthesis for Circulatory Support", ASAIO Journal, vol. 43, pp. M434-M441.

One-Page International Search Report for PCT/US2004/18299, mailed Oct. 5, 2004.

* cited by examiner

DEFORMING JACKET FOR A HEART ACTUATION DEVICE

RELATED APPLICATIONS

This application is a continuation of PCT/US2004/018298 filed on Jun. 9, 2004, which claims priority of U.S. Provisional Patent Application No. 60/477,086, filed Jun. 9, 2003. The disclosure of each priority application is hereby incorporated by reference herein in its entirety.

This application is also a Continuation-In-Part application of U.S. patent application Ser. No. 10/667,877, filed Sep. 22, 2003 now abandoned and entitled "Basal Mounting Cushion Frame Component to Facilitate Extrinsic Heart Wall Actuation" and also is a Continuation-In-Part application of U.S. patent application Ser. No. 10/197,973, filed Jul. 18, 2002 now abandoned and entitled "A Protective Sheath Apparatus and Method for Use with a Heart Wall Actuation System for the Natural Heart," both applications of which are hereby incorporated by reference in their entireties.

FIELD OF THE INVENTION

This invention relates generally to assisting the natural heart in operation and, more specifically, to components to assist in actuating one or more walls of the natural heart.

BACKGROUND OF THE INVENTION

The human circulatory system is critical for survival and systematically provides nutrients and oxygen as well as removing harmful waste products from all parts of the body. The heart is a critical component of the circulatory system in that it provides pumping power. Generally the right side of the heart receives blood from the 'systemic circulation' (all the body except the lungs) and pumps it into the 'pulmonary circulation' (lungs), whereas the left side of the heart receives blood from the lungs and pumps it back into the systemic circulation. Each side comprises an inflow or collecting chamber with a thin muscular wall, its 'atrium' and a thicker, more powerful muscular pumping chamber, its 'ventricle', which alters volume cyclically due to contraction and relaxation of the muscles in its walls. One-way valves are positioned in the passage way between the left and right atrium and the corresponding ventricle, and between each ventricle and the large arteries, which conduct blood into the systemic or pulmonary circulation, respectively. Because of this arrangement, each atrium may gently contract, causing blood to flow across the 'atrioventricular' valve into the ventricle, with that valve then closing to prevent return. Similarly, each ventricle may then forcefully contract, causing blood to flow across the outflow valves into the systemic or pulmonary circulation. A physical ailment or condition which compromises the effective muscular contraction in the walls of one or more chambers of the heart can therefore be particularly critical and may result in a condition which must be medically remedied if the person is to long survive.

More specifically, the muscle of the heart may degrade for various reasons to a point where the heart can no longer provide sufficient circulation of blood to maintain the health of a person at an acceptable level. In fact, the heart may degrade to the point of failure and not been be able to sustain life. To address the problem of a failing natural heart, solutions are offered to maintain the circulation. Some of these solutions involve replacing the heart. Some involve assisting it with mechanical devices. Some are directed to maintain operation of the existing heart.

The heart may be removed and replaced with either a mechanical device (a total artificial heart) or a natural heart from another human or an animal (heart transplant). Artificial heart use has been complicated by consequences of blood clots forming on the internal lining. The most serious consequence is a breaking loose of such clots, which are then propelled into various parts of the circulation. In the event of such a clot being propelled into the brain, a disabling or fatal stroke may result. While human heart transplantation is limited by rejection, a response of the body's immune system, this may usually be controlled by medications to the degree that half of all recipients survive at least ten years, generally with acceptable health and function. However a more serious limitation is numbers of available donors. These are usually accidental death victims whose hearts maintain function despite brain death. Currently these are available for less than 1 to 2 percent of potential beneficiaries (about 2000 per year in the United States for over 200,000 people dying of heart failure annually in the same country, for example).

The heart may be assisted by mechanical auxiliary pumps. These are of three general types: counterpulsators, pulsatile assist systems, and nonpulsatile assist systems. Counterpulsators such as intraaortic balloon pump cyclically remove or displace blood from the arterial system in synchrony with the natural heart's beat and, without valves, may perform substantial work for a weakened heart. Pulsatile assist systems (ventricular assist devices) are similar to artificial hearts except that they are used in addition to one or both sides of the heart rather than instead of the heart. They receive blood from either the atrium or ventricle on one side of the circulation and pump it into that side's arterial system, relieving the ventricle of part of its volume load, pressure load, or both. They consist of a blood chamber with at least partial wall flexibility, inflow and outflow valves, and some means, usually pneumatic, hydraulic, or electric, by which the wall may be moved and volume altered to pump blood. Nonpulsatile assist systems are rotary pumps, either centrifugal, axial flow, or a combination, that similarly pump blood in a steady flow from atrium or ventricle into circulatory systems. All of these mechanical pumps have extensive non-living material surfaces that contact blood. The complications of blood clotting with stroke or other serious aftermaths described with artificial hearts also occur with these mechanical auxiliary pumps.

Because of the severe shortage of human donor hearts for transplant, unsolved immunologic problems of animal donor hearts for transplants and prevalence of serious complications of artificial blood-contacting surfaces of both artificial hearts and auxiliary pumps, means of aiding the actuation of the natural heart walls have been attempted. Both skeletal muscle wraps ('cardiomyoplasty') and mechanical compression devices ('mechanical ventricular actuation') have been used. In either approach, the external wall surfaces of the heart are compressed and the heart volume altered, thereby pumping blood out of the chambers. Muscle wraps are limited by available space relative to muscle mass required for power, as well as by intrinsic stiffness that compromises re-filling between beats. Both muscle wraps and mechanical compression devices are limited by inability to effectively restrict volume and pressure delivery to one chamber of the heart. This chamber restriction is important because the two sides of the circulation require far different pressures for acceptable function (usually the systemic pressure is 3 to 5 times as high as is the pulmonary pressure). Compressive patterns of either muscle wraps or mechanical devices may also distort heart valves, which can lead to valve leakage.

Therefore, to be effective and safe, mechanical pumping of a person's existing heart, such as through mechanical compression of the ventricles or some other action thereon, must address these issues and concerns in order to effectively and safely pump blood. Specifically, weakened ventricle or ventricles must rapidly and passively refill between beats at low physiologic pressures, and the valve function must be physiologically adequately. The blood flow to the heart muscle must not be impaired by the mechanical device. Still further, the left and right ventricular pressure independence must be maintained within the heart.

Internal stabilizing components to complete the three-dimensional control of a chambers' boundaries, which components are suspended through the substance of heart walls from the external (to the heart) actuating mechanism should be a useful adjunct. These provide a means to facilitate the precise control of actuation—determining the prescribed pattern and distribution needed to (1) prevent valvular distortion, (2) avoid myocardial blood flow compromise, (3) provide a type of shape alteration of the actuated chamber at end-actuation which will facilitate passive refilling during shape restoration, and (4) ensure relative independence of pressure in the various chambers.

Specifically, U.S. Pat. No. 5,957,977, which is incorporated herein by reference in its entirety, discloses an actuation system for the natural heart utilizing internal and external support structures. That patents provides an internal and external framework mounted internally and externally with respect to the natural heart, and an actuator device or activator mounted to the framework for providing cyclical forces to deform one or more walls of the heart, such as the left ventricular free wall. The invention of U.S. patent application Ser. No. 09/850,554, which has issued as U.S. Pat. No. 6,592,619, further adds to the art of U.S. Pat. No. 5,957,977 and that patent is also incorporated herein by reference in its entirety. The application specifically sets forth various embodiments of activator or actuator devices, which are suitable for deforming the heart walls and supplementing and/or providing the pumping function for the natural heart.

While the actuation systems of those patents provide a desirable actuation of the natural heart, it is further desirable to improve upon the interface between the actuation system and the heart.

Specifically, the coupling between the internal and external framework elements of the actuation system occurs across tissue. For example, transmural cords extend between semi rigid internal valve annular rings and an external transverse arc of a yoke coupled to the outside of the heart. Due to over-tightening of the cords when they are positioned, and/or to swelling of the tissue afterward, there may be compression of myocardial tissue and traversing of coronary artery branches.

Also, the coupling between discrete actuating components and discrete framework components, both external to the heart, have potential of damaging or abrading the surface of the heart during motion.

It is further desirable to achieve such goals while still providing sufficient anchoring for the various components of the actuation system. It is still further desirable to provide a counterforce to stabilize the base of the ventricular mass during application of deforming forces to the free walls and/ or septum of the ventricle or ventricles.

Still further, it is an objective to provide desirable actuation of the heart to achieve a long-term solution to heart weakening or heart failure. These objectives and other objectives and advantages of the present invention will be set forth and will become more apparent in the description of the embodiments below.

BRIEF DESCRIPTION OF THE DRAWINGS

The active jacket is a preferred embodiment of the basal cushion, which extends over the free ventricular wall of one or both ventricles as well as over the ventricular base. In this embodiment, it is a thin (generally 0.5 to 8.0 mm thick), flexurally elastic jacket substantially encompassing the epicardial surface of at least one chamber of the natural heart. 'Flexurally elastic' in this description is defined as having a measurable bending stiffness (neither flaccid nor absolutely rigid) in a tangent plane in at least part of the structure. Fabrication methods and materials may be varied as required in any location to meet required specifications. The jacket may also be longitudinally elastic in tension and/or compression in at least one direction at one or more locations.

FIG. 11A is an elastic tension-indicator with two suture ends loosely looped through.

DETAILED DESCRIPTION OF EMBODIMENTS OF THE INVENTION

For the purposes of illustrating the invention, the following parts list corresponds to the Figures listed above and included herewith.

Figure 1:
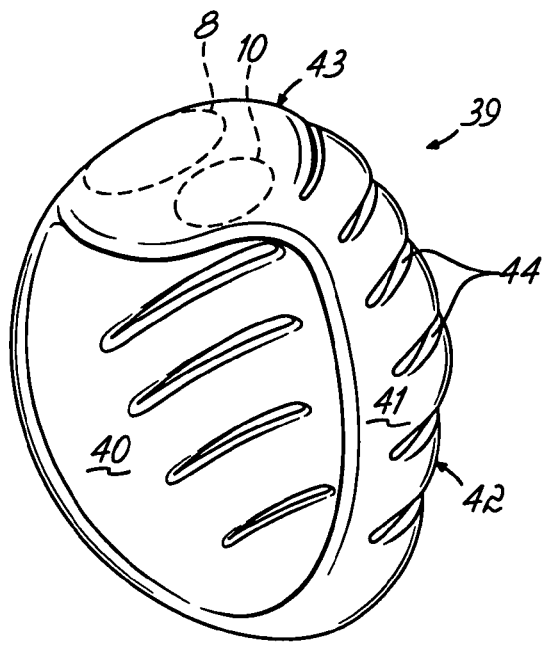
FIG. 1 is a non-limiting example of an active jacket configured for the left ventricle, alone.

Part Numbers
1. - - -
2. Left ventricle
3. Right ventricle
4. Left atrium
5. Right atrium
6. Aorta
7. Pulmonary artery
8. Opening or aperture for the left atrium
9. Opening or aperture for the right atrium
10. Aperture for aorta
11. - - -
12. - - -
13. Aortic sleeve: a protective tubular extension along the external surface of the proximal aorta. This provides a smooth surface over vulnerable area of the aortic sinuses and proximal coronaries.
14. - - -
15. Mitral valve
16. - - -
17. - - -
18. - - -
19. Proximal right coronary artery
20. Right coronary cusp of the aortic valve, shown in section through its center
21. - - -
22. Aortic wall, shown in longitudinal section
23. Commisures between left coronary cusp and the noncoronary cusp of the aortic valve
24. Noncoronary cusp of the aortic valve
25. - - -
26. Left coronary cusp of the aortic valve
27. Proximal left coronary artery
28. Septal leaflet of the tricuspid valve
29. - - -
30. - - -
31. Conventional type of mitral annuloplasty ring
32. Desirably compressed region
33. Excessively compressed region
34. - - -
35. - - -
36. - - -
37. Actuator system
38. Actuator element
39. Jacket
40. Inner (heart-facing) surface
41. Outer surface
42. Free wall part
43. Basal part
44. Fenestrations
45 Serpentine spring wire pattern
46. Polymer padding, composed preferably of polyester fiber, which may be impregnated with an elastomer such as silicone rubber or a urethane.
47. Woven serpentine wire
48. Textured region of inner surface
49. Atrial collar
50. Sutures exiting from base of right side septal support
51. Sutures exiting from lateral margins of right side septal support
52. Patch repair for atrial separation
53. Aortic root
54. Clear first layer
55. $2^{nd}$ layer, thin soft elastomer that may have suspended colloid or gas to increase diffusion except when compressed
56. $3^{rd}$ layer, transversely cross hatched
57. $4^{th}$ layer, thick soft elastomer, either thicker or somewhat less soft than $2^{nd}$ layer
58. $5^{th}$ layer, vertically cross hatched
59. Region indicating safe range of underlying compressive stress
60. Region indicating unsafely high range of underlying comprehensive stress
61. Jacket region that is being secured
62. Elastic loop
63. Gradations for tightness
64. Region indicating too loose
65. Region indicating too tight
66. Suture ends with one loose knot
67. Suture ends with knot tightened correctly
68. Tubular portion of great vessel sleeve
69. Flared portion of great vessel sleeve
70. Asymmetric region of the flared portion in which spherical particles are enclosed in a "bean-bag" arrangement
71. Surrounding region of basal section of active jacket
72. - - -
73. Suture line of patch to right atrial wall
74. Margin of active jacket
75. Separation and reattachment point in jacket margin to facilitate placement on an intact heart
76. Tubular portion of atrial collar
77. Shingle of atrial collar
78. Circumflex coronary artery
79. Coronary sinus
80. Left ventricular free wall
81. Left atrial wall
82. Posterior leaflet of the mitral valve
83. Anterior leaflet of the mitral valve
84. Sutures fixing annuloplasty ring to collar through atrial wall
85. Interventricular septum
86. Outflow tract of left ventricle
87. Polymer mesh
88. Elastomeric polymer
89. Atherosclerotic plaque
90. Separation and re-attachment point on basal section of jacket In one embodiment of the present invention, a cushioned, flexurally elastic jacket is configured to rest on the extracardiac border of at least one cardiac chamber, including the basal margin. FIG. 1 is a non-limiting example of such an active jacket [39] configured for the left ventricle alone.

The jacket has an inner, or heart-facing surface [40] and an outer surface [41]. The jacket generally has a free-wall [42] section and a basal section [43] each of which may extend over the left, right, or both sides of the heart—although the illustration in figures shown is for the left ventricle. The free-wall section of the jacket is configured to fit over the free wall of the ventricle, and the basal section over the ventricle's base, surrounding its inflow and outflow valves.

The free-wall section of the jacket [39] may include one or more actuator elements [38], such as mechanical actuator elements, for deforming the free wall section to assist or replace the natural operation of the heart. The actuator element [38] will be coupled to a suitable actuator system [37] for providing the power and control of the actuation, such as to exert a force and empty the heart chamber (systole). The free-wall section of the jacket, whether part of a left, a right, or biventricular device, since it has flexural elasticity as described above, exerts an outward force on pericardium or other tissues surrounding the ventricular free wall during refilling (diastole). This is due to passive elastic recoil derived from energy stored during active ejection(systole). The outward force may be transmitted to the heart wall, and thus assist refilling either by means of a relative vacuum produced between the jacket and heart wall (following chest closure and removal and/or absorption of any air or free fluid) or by means of direct adhesion of the heart wall to the jacket during healing.

While it shares similarities of employing spring strain energy, stored in systole, to assist diastolic filling, these embodiments of the active jacket are distinguished from an embodiment of the 'spring-loaded ventricle' concept disclosed through CardioClasp, Inc. in that in all embodiments of that disclosure, restoring force was directly applied to the inside the heart chamber. The active jacket of the present invention is completely outside the ventricle.

The jacket preferably has means provided for egress of tissue fluid that may accumulate, either discrete fenestrations [44] or porosity of at lease part of the structure. The basal portion has either pre-cut apertures for the great vessels and atria or is suited for cutting these as required at operation. In the non-limiting example shown, dashed lines indicate sites of the aperture for the aorta [10] and of the aperture for the left atrium [8].

Figure 2:
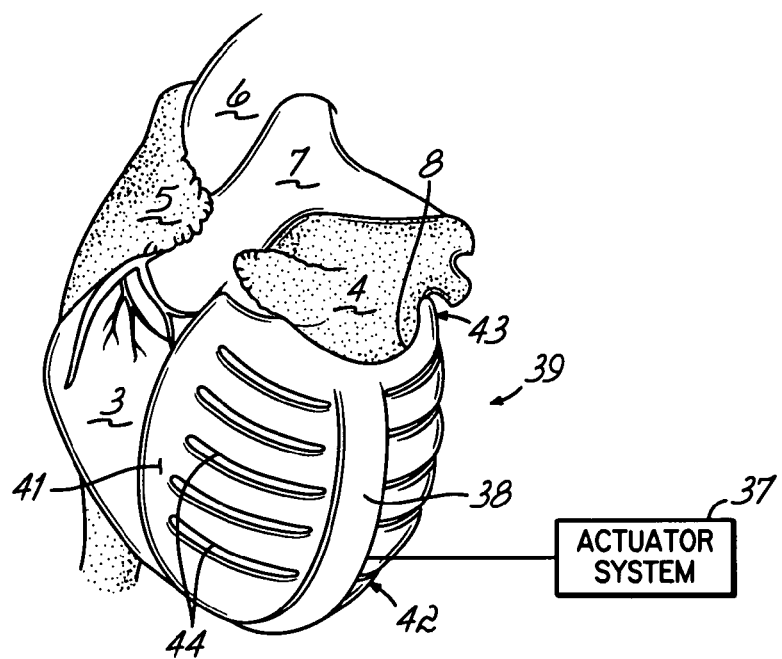
FIG. 2 is the same jacket in place on an intact heart in diastole.

FIG. 2 shows the same jacket in place on an intact heart in diastole. Those parts labeled in FIG. 1 are similarly labeled in FIG. 2. The left ventricle is obscured by the jacket in FIG. 2. The free-wall part of the jacket extends to the margins of the right ventricle [3]. The basal part surrounds the left atrium [4] and aorta [6], with the margins of this part extending between the left atrium [4] and right atrium [5] as well as between the aorta [6] and pulmonary artery [7].

Figure 3:
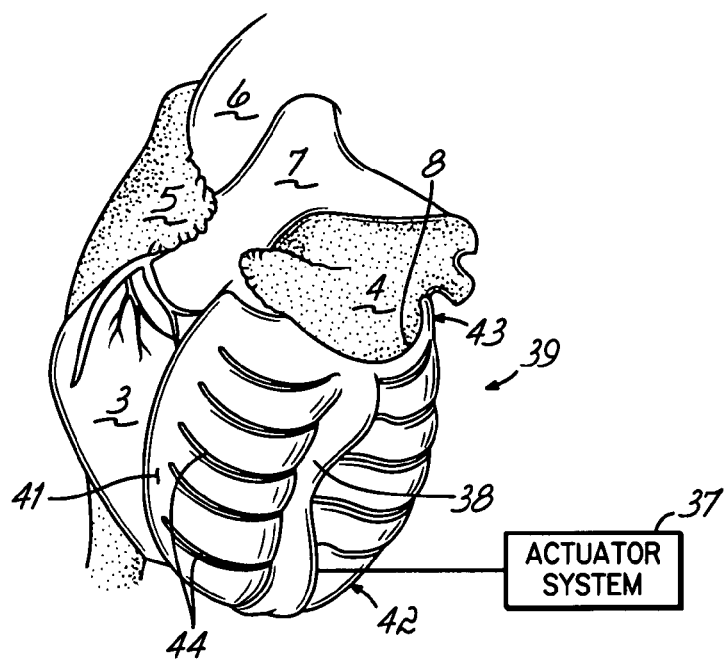
FIG. 3 is the jacket in place on an intact heart in systole.

FIG. 3 shows the jacket in place on an intact heart in systole, parts are labeled the same as in FIG. 2.

Figure 4:
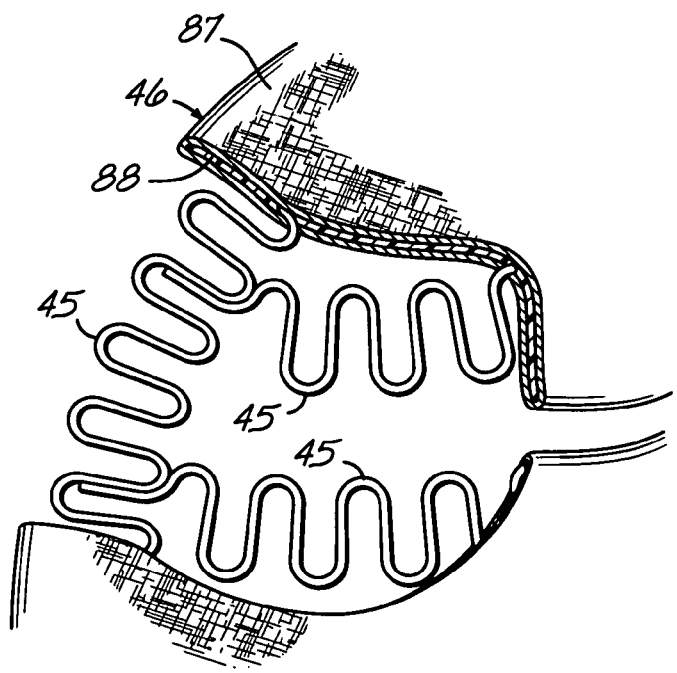
FIG. 4 is a preferred embodiment in which a serpentine pattern spring wire grid structure is clad in polymeric padding.

Mechanical characteristics of the jacket may vary at various sites within the jacket. That is, the jacket may be, but is not necessarily, isotropic and/or homogeneous in structure. The ventricular portion of the jacket is preferably not obstructive to through-flow of tissue fluid, allowing any such fluid accumulating near the heart to exit and thus be more likely to be reabsorbed. The jacket may be fenestrated in multiple places as shown in FIG. 1 and FIG. 2 to allow egress of tissue fluid or the jacket may be diffusely porous to tissue fluid. The jacket's flexural elasticity may be imposed by spring elements that make up part or all of its structure. The spring elements are preferably metal that both is biologically minimally reactive and possesses a defined 'endurance limit', meaning a level of tensile, compressive, or shear stress which may be repetitively imposed for an infinite number of cycles without fatigue failure. Examples are commercially pure titanium, nickel-titanium alloy (Nitinol), and several types of stainless steel. FIG. 4 shows a preferred embodiment in which a serpentine pattern spring wire grid structure [45] is clad in polymeric padding [46], composed preferably of a polymer mesh [87], such as polyester, which is in turn impregnated with a soft elastomer [88] such as silicone rubber.

Figure 5:
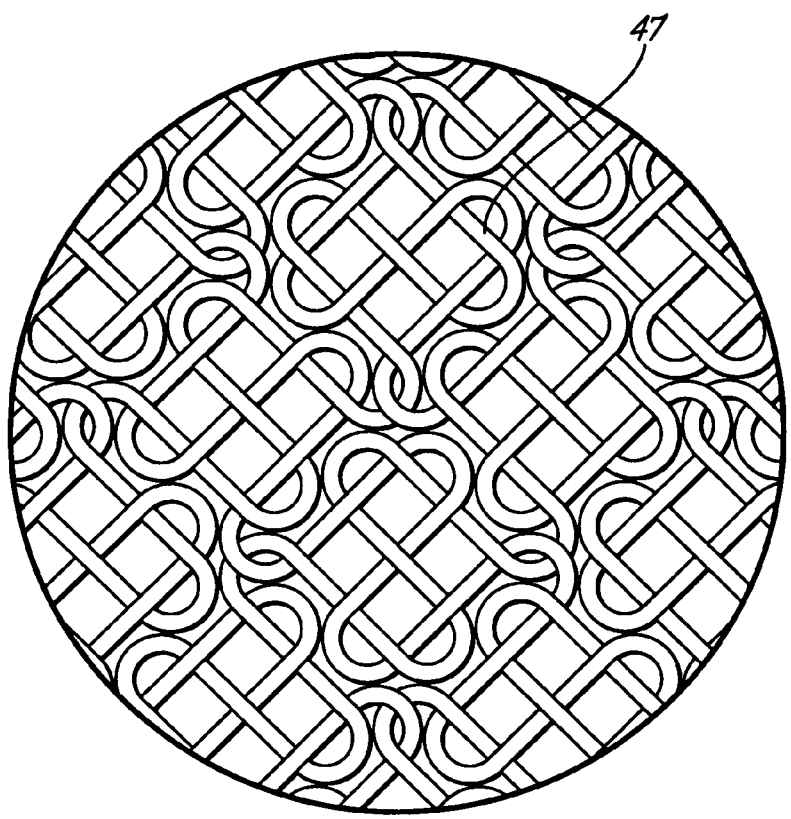
FIG. 5 is a nonlimiting example showing close detail of an alternate construction in which spring elements make up all of the jacket's structure.
Figure 6:
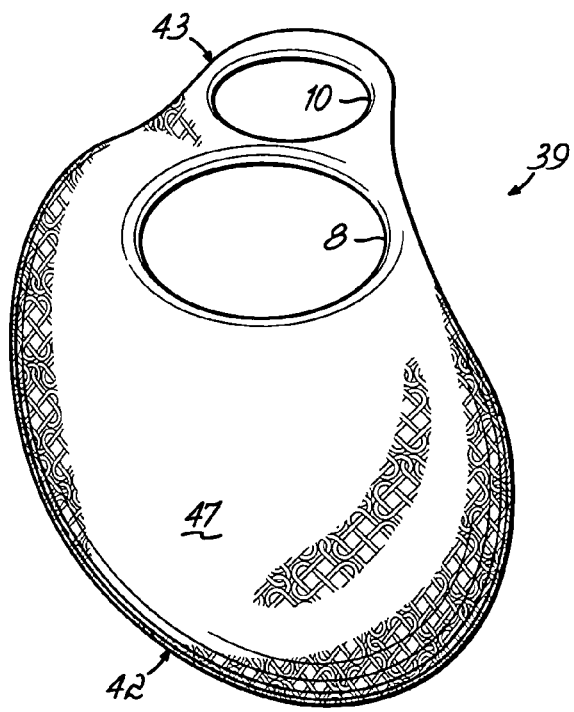
FIG. 6 is a whole jacket for left ventricular application of the structure shown in FIG. 13.

A nonlimiting example of an alternate construction in which spring elements make up all of the jacket's structure is shown in FIGS. 5 (close detail) and 6 (whole jacket for left ventricular application); the network of spring elements is generally finer than in embodiments in which a composite fabrication is used. In the non-limiting example shown here, fine serpentine wire [47] is woven, knitted, braided or otherwise enmeshed, with or without local welding or adhesion into a jacket having a free-wall section [42] and a basal section [43], with the basal section have a left atrial and mitral aperture [8] and an aortic aperture [10].

This (the all-spring active jacket) is distinctly different from the structure of some superficial similarity that is taught by International patent publication # WO 01/67985 A1 and precedent US filings, by Lau, assigned to Paracor, Inc. The Paracor filings teach a mesh made up of linked individual spring units in such as way that it purposefully does not have the defined flexural elasticity of the active jacket taught herein, but is instead flaccid to flexion, as is appropriate for it's completely different purpose (anisotropic passive restraint of a dilated heart).

The spring elements may alternatively be made of nonmetallic materials such as glass fibers, carbon fibers, composites of such fibers with matrix materials such as an epoxy or polyester compound, or other materials—either single composition or composite—with similar mechanical and biologic properties.

The spring elements may be of any configuration known to those familiar with mechanical design, such as ribbon, leaf, corrugated sheet, coil, bar, or serpentine wire, with present preference being serpentine wire. Mechanical behavior of either the entire jacket or portions of it may be altered by design by varying the number of spring elements, joining techniques between spring elements, the distribution and orientation of spring elements, thickness or gauge of materials, and spring configuration at any site. In the presently preferred embodiment of serpentine wire metal spring elements, "configuration" in this context means periodicity of undulations, amplitude of undulations, and the pattern (that is, whether the pattern is sinusoidal, continuous link of circular arcs with or without straight segments, and so forth).

The jacket may be partially or totally constructed of soft materials, which contribute all, or part of its flexural elasticity. These soft materials may be polymer fibers (such as polyester) (either unorganized or organized in some fashion such as a braid, weave or knit). In an alternative, these soft materials may be an elastomeric polymer (such as silicone rubber or a polyurethane).

In yet another alternative, the soft material may be a fiber structure such as described above, impregnated with an elastomeric polymer such as also described above, so as to form a fiber-reinforced, elastomeric-matrix composite. The jacket may be comprised of multiple materials such as spring elements of the types described above in a network encased in soft materials such as the polymer fibers, the elastomeric polymer, or the composite of both described above.

Figure 12:
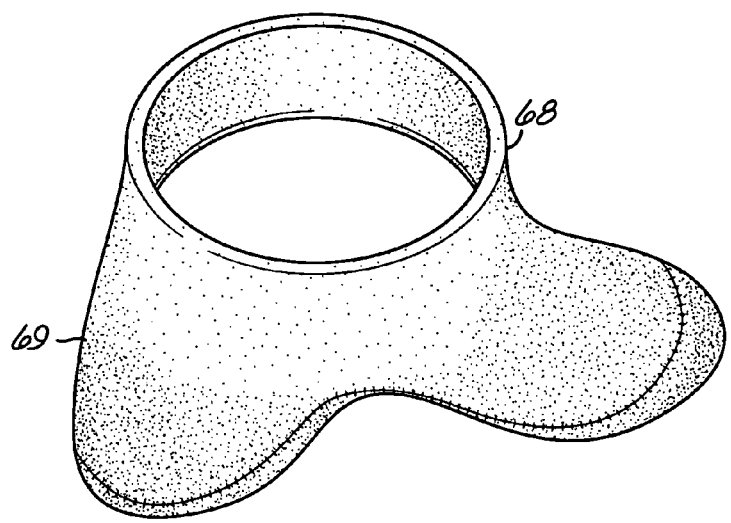
FIG. 12 is a great vessel sleeve in perspective view.

A preferred embodiment of composition, shown in a non-limiting example in FIG. 12, employs titanium serpentine springs that are clad in polyester mesh and then vacuum impregnated with silicone rubber.

Figure 7:
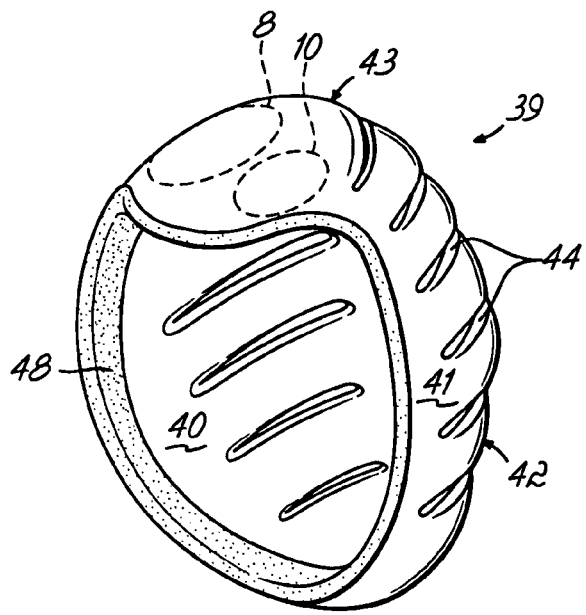
FIG. 7 shows a textured region on part of the heart-facing surface of a jacket.

The jacket may have additional cushioning, such as a layer of very low durometer elastomer, over all or part of its inner surface At least part of the jacket's inner surface may be textured so as to encourage adhesion to the heart wall during healing. Regions of the inner surface may have additional cushioning or texturing or both or neither. Texturing with a material such as polyester velour, overlaying or incorporated in all or part of the jacket's inner surface, in intended to encourage secure adherence to heart surface during healing. This is shown in FIG. 7, including the textured area [48]. The jacket may have a smooth membrane, such as silicone or polyurethane, overlaying or incorporated in its inner surface to discourage tissue adhesion and encourage a thin, flexible, stable, and mobile fibrous encapsulation.

In the preferred method of seating the jacket on a heart, the needles of the completed circumferential row of sutures or cords, extending from bolsters, framework or other means of interventricular septum stabilization, are, after exiting the ventricular or atrial external surfaces, advanced through the substance of the jacket near its margin, following by lowering the jacket into place and tying in a manner used by and familiar to cardiac surgeons for sewing and seating a prosthetic heart valve. Protective structures, such as those described below, for the great vessel(s) and atrium(or atria) are placed prior to lowering the jacket into position and tying the sutures, which secure the jacket.

Figure 8:
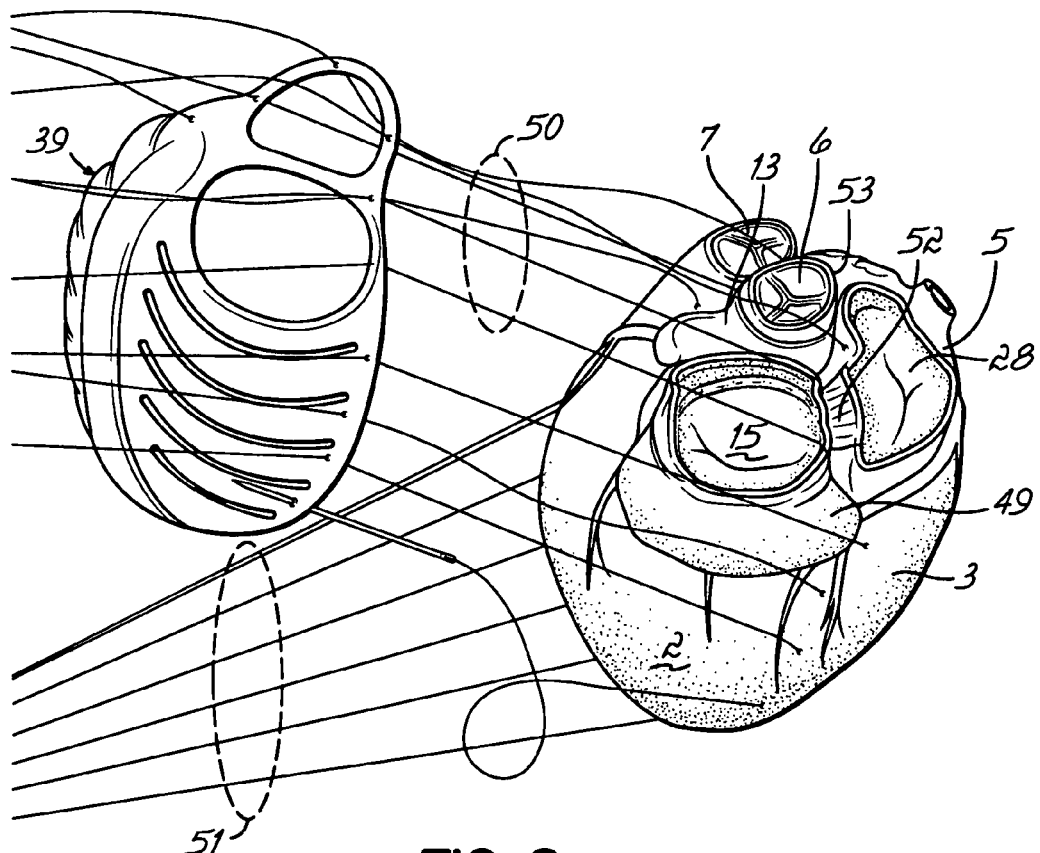
FIG. 8 is a left-side device jacket suspended above the heart while sutures exiting from internal septal-supporting components are placed circumferentially in the margins of the jacket, both its free-wall and its basal sections.

FIG. 8 shows a left-side device jacket suspended above the heart while sutures exiting from internal septal-supporting components are placed circumferentially in the margins of the jacket, both its free-wall and its basal sections. A repair patch [52] for atrial separation has been placed, repairing the medial wall defect in the right atrium after separation from the interatrial septum. This maneuver is required for the basal jacket margin to securely support the mitral annulus and/or, in a biventricular or right side device, the tricuspid valve. The aortic sleeve [13] and the left atrial collar [49], both protective structures, have been placed (these are described in detail below). Sutures [50] originating from the basal margin of the septal support components (either those described in U.S. Pat. No. 5,957,977 or others disclosed and filed separately) exit through the sub-tricuspid space, the roof of the conus portion of the right ventricle, and the septal margin of the pulmonic valve. Sutures [51] originating from free wall part of the septum exit through the anterior and posterior free-wall/septal angles of the right ventricle [2]. As the jacket is lowered into place, margins are brought to rest between the separated atrium adjacent the tricuspid valve [28] and enclosing both the left atrium [4] mitral valve [15] as well as the aortic root [53]. At least most of the free wall of the left ventricle [2] is supported.

Figure 9:
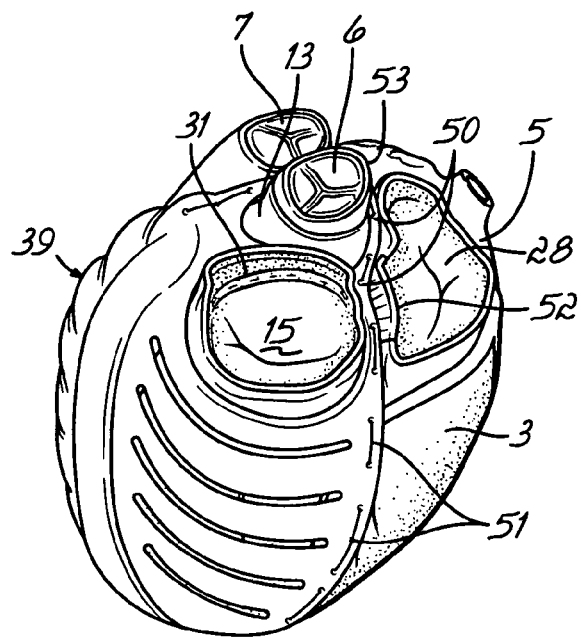
FIG. 9 is the device of FIG. 16 after it has been lowered into position with sutures tied or otherwise secured.

FIG. 9 shows the jacket after it has been lowered into proper position and the sutures tied. Part numbers are the same as for FIG. 8. Both of these illustrate a left-side only device, as a nonlimiting example. The procedure for a right-side only is analogous in each step, whereas in a bilateral device all components except the right free-wall section are placed in a procedure identical to that illustrated (noting that the basal section will in that event extend over the whole base, including the right atrium and pulmonary artery root); right free wall section components are subsequently attached to the left free wall section.

In a modified similar method, the sutures are mechanically fixed, rather than tied, to prepared receiving elements in the jacket near its margins.

Because of the risks of tying or fixing these jacket-fixing sutures or cords either excessively loose (i.e., bleeding from the heart surface) or excessively tight (i.e., reduction of blood flow to the heart tissue supplied by any coronary arteries traversing the region), means of measuring or otherwise controlling the tension with which these sutures or cords are placed may be useful. The teaching of this invention includes examples of such means.

An indicator device may be used with, calibrating tightness of tied sutures joining internal structures, such as bolsters or frame struts, through myocardium to jacket. The indicator device may function as a surface tension indicator to allow control of suture tying tightness in which a laminated structure, with alternate laminae translucent and either textured or colored, in such a way that a visible change signals achievement of adequate tightness for control of bleeding. This indicator system may be constructed in such a way that a visible change signals achievement of excessive tightness that, if not reversed, could risk tissue damage.

Figure 10A:
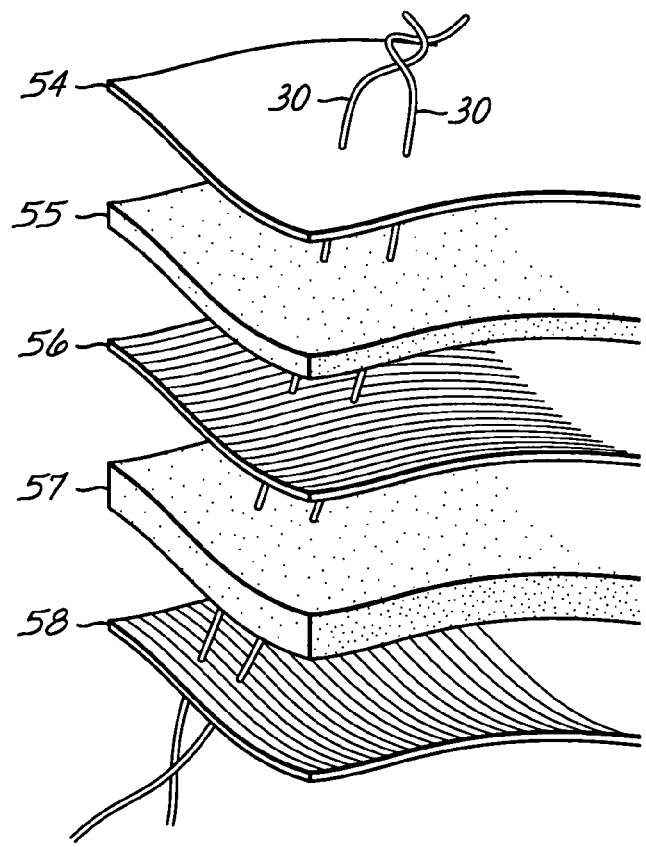
FIG. 10A is a laminar tension-indicator surface shown in exploded view.
Figure 10B:
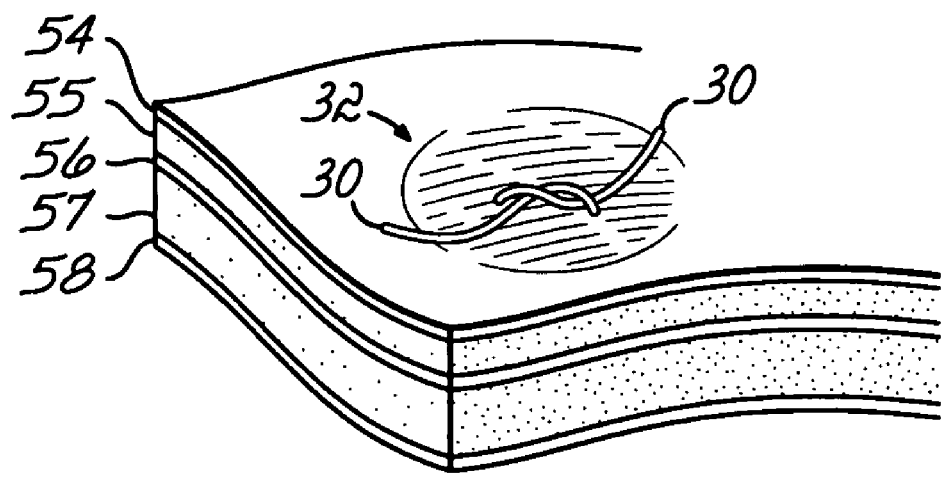
FIG. 10B is a laminar tension indicator with a suture tied sufficiently tight.
Figure 10C:
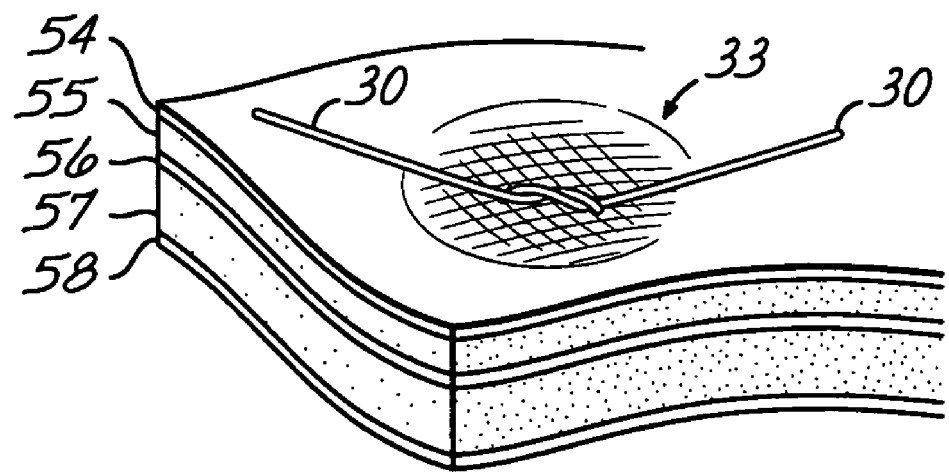
FIG. 10C is a laminar tension-indicator surface with a suture pulled excessively tight, indicating need to loosen before completing knot.

A specific example of such a system follows, as illustrated in FIGS. 10A, 10B, and 10C. The jacket may be equipped on part or all of its outer surface with a translucent layered composition structured so that tying of a penetrating suture [30] results in a local color or other visible change that is at least semi quantitatively related to the tightness of tying and thus to the compressive stress being imposed on the underlying heart surface. A nonlimiting example is a laminar structure in which the first, third, and fifth layers [parts 54, 56, and 58] are transparent and either colored yellow, blue, and red, respectively, or having none, left-to-right cross-hatches, and up-to-down crosshatches, respectively, with the first layer [54] being the outer surface. Each of these layers are of a thin elastomer with the appropriate pigment or pattern added, and preferably reinforced with a fine polymer fiber mesh to enhance tear resistance. Between the first and third layers, the second layer [part 55] is a very thin layer of extremely low durometer (e.g., an order of magnitude softer than the pigmented or cross-hatched layers) clear elastomer, and between the third and fifth layers, the fourth layer [part 57] is similar to the second layer except either for being thicker, firmer, or both—and thus less easily compressed. The second and fourth may contain suspended colloidal particles or gas bubbles so as to increase light diffusion and thus decrease transparency when not substantially compressed. This structure will provide an indicator of the compressive force of a tied penetrating suture loop. The mechanism is that a certain degree of compressive stress will cause sufficient thinning of the second layer that the initially visible yellow surface color becomes green as it becomes compressed against the blue layer, and then brownish gray as the three indicating layers (the first, third, and fifth) are all closely compressed by the thinning of the second and fourth layers. In the lined variant, thinning of the second layer with pressure causes the non-lined appearance of the first to transform locally to the left-to-right crosshatching as the third layer becomes visible through it, and by a similar process at still higher tying pressure then transforms to a grid pattern as the fifth layer also becomes visible from the surface in the immediate vicinity of the suture being tightened. Thus a desirably compressed region [32] and/or any excessively compressed region [33] will be readily recognizable. As will be apparent, for either variant construction parameters may be selected such that the yellow to green (or clear to lined) transition occurs at a compressive stress which in the underlying tissue is expected to arrest bleeding, while the green to brownish-gray(or lined to gridded) occurs at a stress somewhat lower than one at which tissue ischemia is risked. This may be calibrated based on experimental assessment to a level where tying 'tight enough but not too tight' is readily achieved by visual guidance.

FIG. 10A is an 'exploded' view of laminar construction as described in the prior paragraph. FIG. 10B illustrates the first transition where single direction cross hatch marks are visible, representing achievement of the 'safe and necessary' pressure, whereas the grid cross hatching in FIG. 10B indicates the point of excessive compressive stress—suggesting the suture be loosened.

Figure 11A:
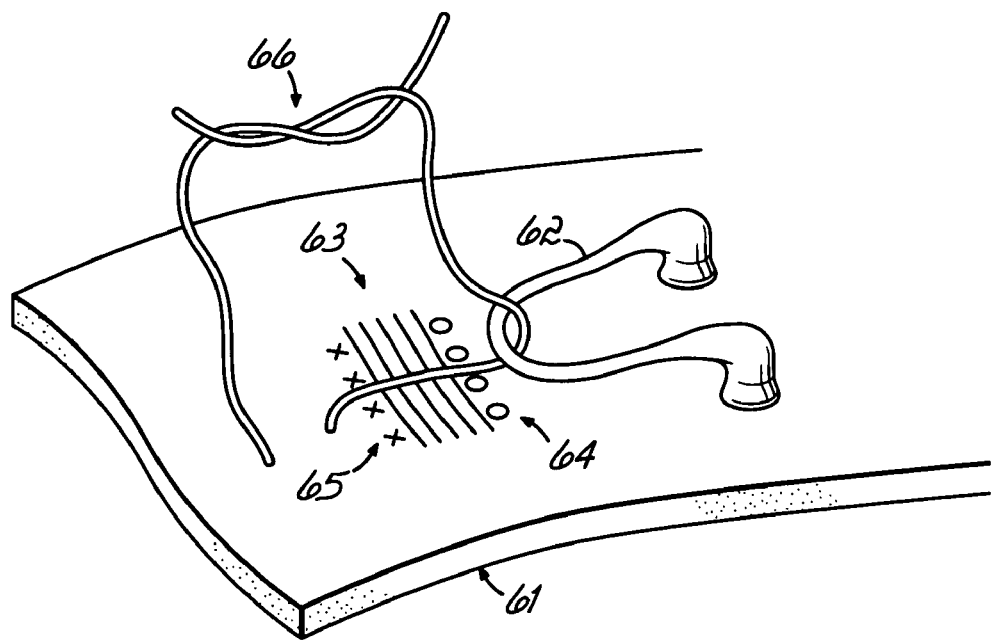
Figure 11B:
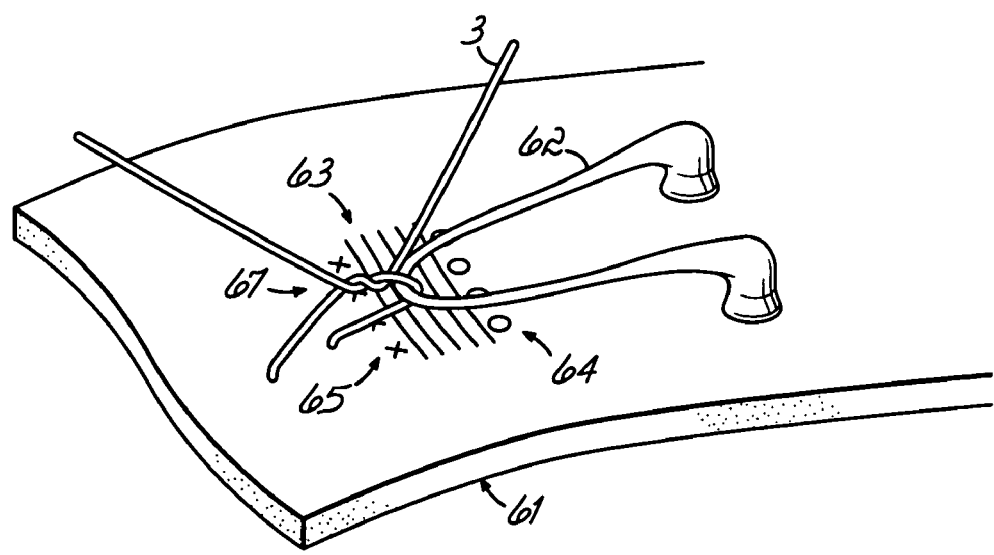
FIG. 11B is an elastic tension-indicator with two suture ends looped through and knot tightened to appropriate tension.

An alternative means of calibrating suture tying tightness while securing the jacket [61] is the tensile elastic element such as a spring of various configurations or a loop [62] of elastomeric polymer such as shown in the nonlimiting example of FIGS. 11A and 11B. This is complemented with visible indicators of the elastic element's extension, and thus tension placed upon it. These indicators may be ridges, grooves, color bands, dashes [63] or other marks and may be labeled with numbers, letters, and so forth. Special markings such as the '0's' [64] may indicate inadequate tension and the 'X's' [65](both in FIG. 11A may indicate excessive tension. The tensile elastic element is based at a short distance from the site of suture penetration and looped by the penetrating suture ends before tying. Deformation may be gauged by marks on the jacket surface to be too loose, as the beginning knot[66] in FIG. 11A or in a range deemed safe as is the knot in FIG. 11B and the knot completed. To avoid cyclic elastic deformation during actuation, which may be undesirable, the established position may be made permanent by any commonly used fixation technique such as another suture, a staple, or a brad, or a combination of these or other techniques and devices to anchor the tied cord or suture to the substance of the jacket at the determined location.

Yet another alternative is use of a tension-calibrating device for fixing sutures which is an adaptation of ratcheted tension-control fastening devices familiar to those in both cardiac surgery and engineering design (e.g. 'snap-band guns') configured to work with sutures after penetrating from bolsters and regulate tension at which sutures are mechanically fixed.

Figure 13:
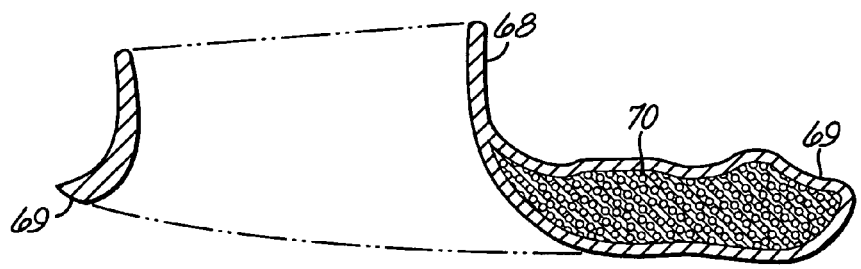
FIG. 13 is a great vessel sleeve in sectional view.
Figure 14:
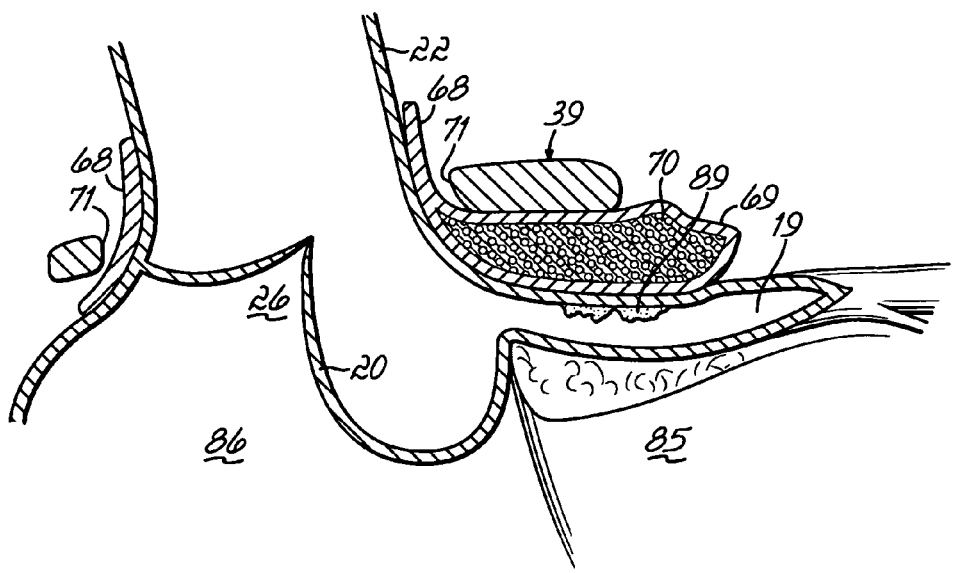
FIG. 14 is a great vessel sleeve in sectional view mounted on the aorta.

The ratcheting and tension limiting features of such devices may be either adapted and incorporated into prefixed openings in the margins of the jacket into which the sutures may be inserted or configured to be used with sutures penetrating the jacket's substance by needles or by other means. An auxiliary structure may be required for stabilization and protection of great vessel origins during and after placement of the jacket. These structures may or may not provide for fixation to the jacket, to the great vessel or to both. For the great vessels, a 'sleeve' may be configured for fitting around the base or root of the aorta or pulmonary artery, the sleeve and the vessel which it surrounds being within that vessel's aperture in the basal portion of the active jacket. The sleeve is illustrated in FIGS. 12 and 13.

The sleeve may have a tubular portion [68] that envelopes the aorta or pulmonary artery for approximately 5 to 40 mm starting near the level of the valve commisures, to be placed after separation of the soft tissue joining the pulmonary artery and aorta.

The tubular portion of the sleeve may be of a biocompatible material, that is porous such as expanded polytetraflurethylene (ePTFE) or knitted or woven polyester. Alternatively, the tubular portion of the sleeve may be of a biocompatible material that is nonporous such as solution cast polyurethane. The tubular portion the sleeve may be complete with intent to place over the proximal part of a transected great artery in the case of a complete or partial autotransplantation placement technique. The tubular portion of the sleeve may be separated vertically at one point on the circumference, preferably at the point that will be over the center of the non-coronary cusp of the aortic valve in the case of aortic use.

The sleeve may have a flared portion [69] that extends outward between the great vessel and the part of the jacket that is adjacent the great vessel aperture. The junction of the tubular and flared portions of the sleeve may be smooth and continuous to conform to the underlying tissue surface. The flared portion of the sleeve [69] may be of a biocompatible material that is in two layers joined at the margins, both porous, such as expanded polytetraflurethylene (ePTFE) or knitted or woven polyester, with solid particles, spherical or otherwise, 1 to 5 mm in diameter, loosely packed between the layers in the fashion of a 'bean bag' [70] so that it will protect the base of the great vessel against potential abrasion by the margins [71] of the active jacket's great vessel aperture(s). This is believed to be particularly important in a left or biventricular system, as the coronary arteries originate from the aorta, as shown by the right coronary artery [19] in FIG. 12, which may be vulnerable and require especially gentle handling in the event of atherosclerotic plaques [89] which are common in heart failure patients who will require such a device.

The flared portion of the sleeve may be composed of a biocompatible material that is in two layers joined at the margins, both nonporous, such as solution cast polyurethane, possibly reinforced with another polymer membrane, with a liquid (such as saline solution or silicone oil) or a gel (such as silicone gel or a biocompatible hydrogel) contained between the layers.

The flared portion of the sleeve may be composed of a biocompatible material that is in two layers joined at the margins, both being asymmetric in the case of the aorta, extending outward in a lobular fashion over the location of the origin of the two main coronary arteries and their more proximal branches in order to protect them from any eroding effect of the margins of the aperture.

An auxiliary structure may be required for stabilization and protection of atrial bases including atrioventricular valve annuli during and after placement of the jacket. These structures may or may not provide for fixation to the jacket, to the atrium, or to both.

Figure 15:
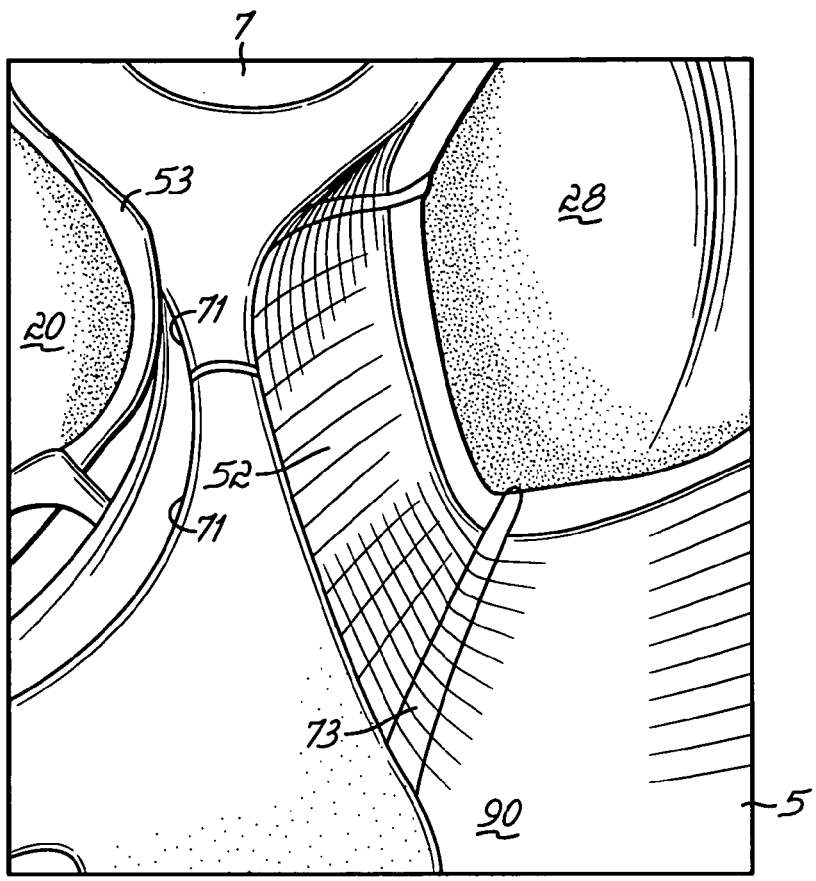
FIG. 15 is patch repair of the medial wall defect in the right atrium that results from separation of the two atria in which the previous intra-atrial septum has been left as a new medial wall for the left atrium.

For stabilization and protection of atrial wall and atrioventricular valve annulus and fixation of those structures to the jacket, a structure termed a 'collar' is taught. A method for preparing the atria for collar placement consists of incising the right atrial wall adjacent the intra-atrial septum and then repairing the resulting defect in the medial right atrial wall with a patch of any material, autologous or prosthetic, which is commonly used for septal defect repair, as illustrated in FIG. 15. The right atrial wall is incised at its junction with the atrial septum, ideally from an extracardiac approach after full dissection through the interatrial fat pad. The incision is carried to the tricuspid annulus anteriorly and posteriorly. The lower margin of a patch [52] of the material selected is then sewn, everted, with mattress sutures to the tricuspid annulus, protecting the septal leaflet of the tricuspid valve [28], and to the base of right atrial side of the previous interatrial septum (which is now the medial wall of the left atrium for a 3 to 5 mm wide broad attachment. The margins are then attached, by, for example, a suture line [73] to the remainder of the right atrial defect. The everted lower lip of the patch provides space in which the margin of the active jacket [71] may rest, with optional separation and reattachment of that margin if the procedure is done on an intact heart [90]. In the event that an explantation and autotransplant technique is used, the separation point in not required, since the intact basal section of the jacket can simply be positioned on the heart before reanastamosis with the posterior atrial margins.

Figure 16A:
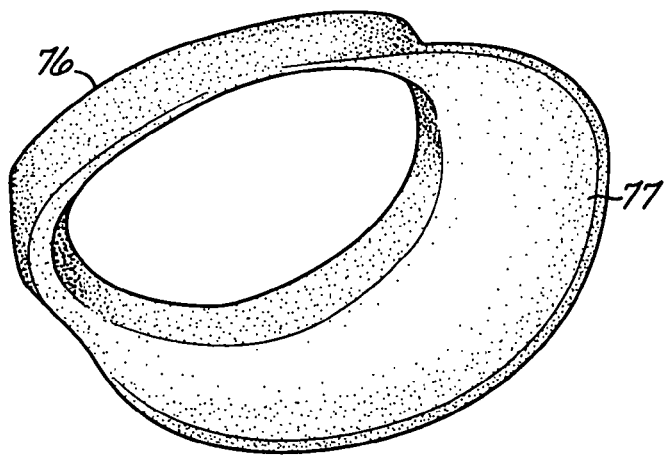
FIGS. 16A-16B are two perspective views of the atrial collar, showing the ventricular (above) and atrial (below) surfaces, respectively.
Figure 16B:
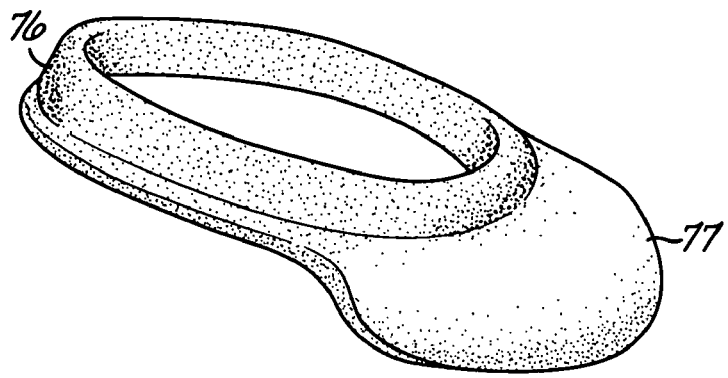
Figure 17:
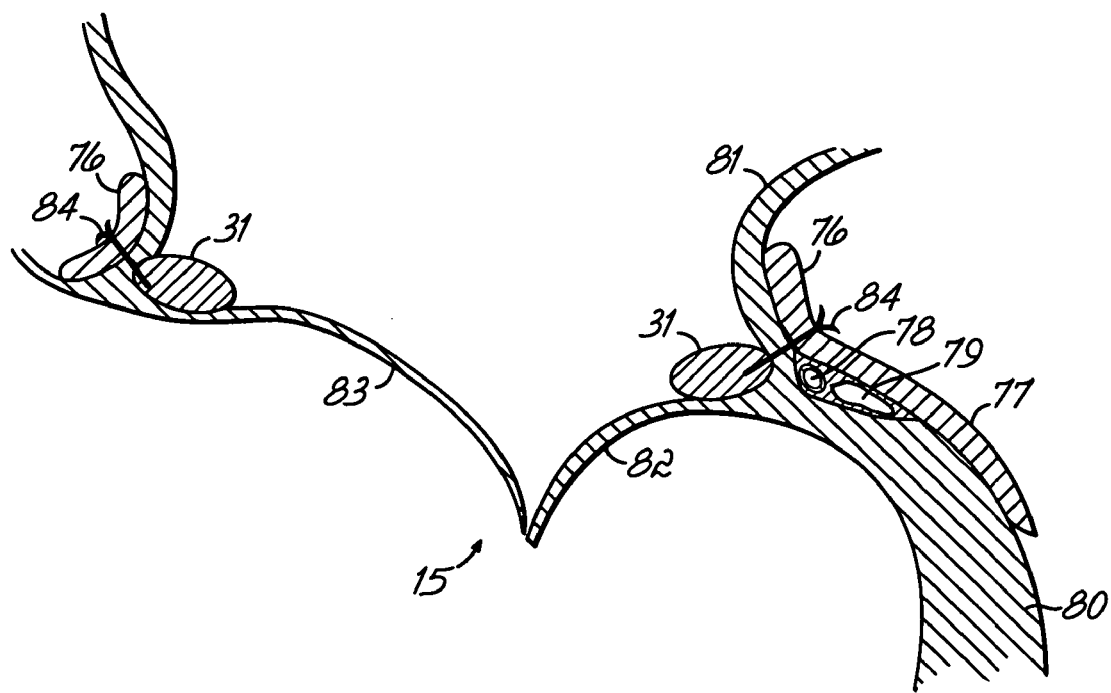
FIG. 17 is a sectional view of the atrial collar on the base of the left atrium.

A collar is configured for fitting around the base of the left or of the right atrium, the collar and the atrium which it surrounds being positioned within that atrium's aperture in the basal portion of the active jacket described above. The collar is illustrated in FIGS. 16 and 17. The collar is made of a flexible thin material having a defined stiffness (i.e., neither flaccid nor rigid), for example a composite of polyester fiber that is knitted or woven or otherwise organized and vacuum impregnated with an elastomer such as low durometer silicone rubber. The collar has a short tubular portion [76] approximately 3 to 10 mm long. The collar has a 'shingle' portion [77], which is smoothly continuous with those parts of the tubular portion exclusive of the prior junction with the contralateral atrium and the region of the great vessel sleeve, and extending outward over the epicardium of the atrioventricular groove, the vessels contained within the fat over the atrioventricular groove, and the adjacent ventricular surface. On the right side the shingle protects the right coronary artery and vein; on the left it protects the circumflex artery [78], the coronary sinus [79] and the adjacent portion of the left ventricular free wall [80]. The left atrial wall [81] flares out above the tubular portion's free margin.

The method of placing the collar is as follows: An annuloplasty ring [31], of standard rigid, semirigid, or flexible type, is fixed onto the mitral annulus using standard operative technique to assure adequate apposition of the posterior leaflet [82] and anterior leaflet [83] of the mitral valve [15]. Then the collar is either slipped over the atrial base intact, in the event of a cardiectomy/autotransplant technique, or separated and reattached in the event of an in situ heart technique. Sutures [84] are placed from the annuloplasty ring through the proximal atrial wall to the collar.

Although the components of the active jacket, the great vessel sleeve, and the atrial collar are each illustrated as individual embodiments, in an alternative embodiment, each of those components might be coupled together. For example, they could be integrally fabricated such that a single structure includes the jacket, the great vessel sleeve, and the atrial incorporated all incorporated in a single element. In another alternative embodiment, while separate pieces, the individual elements might be interlocked such as with interlocking surfaces. For example, mating hook and loop fastening surfaces might be utilized on the heart-facing surface of the jacket for a short distance (a few millimeters) adjacent the aortic aperture and on the away-from-the-heart surface on the flared portion of the aortic sleeve.

While the present invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of applicant's general inventive concept.

What is claimed:

1. A device for assisting in the operation of the natural heart, comprising:
   an external jacket configured for engaging an outer area of a chamber of the heart, the jacket including a free wall section external to the heart and configured for engaging a free wall of the heart chamber and a basal section external to the heart and configured for engaging a base of the heart chamber;
   the basal section including at least one aperture for accommodating an atrial chamber of the heart and at least one aperture for accommodating a great vessel of the heart;
   a sleeve configured for engaging and surrounding a great vessel of the heart and a portion of the sleeve dimensioned to pass through the aperture in the jacket that accommodates the great vessel;
   a collar configured for engaging an atrial chamber of the heart and a portion of the collar dimensioned to engage the aperture in the jacket that accommodates the atrial chamber;
   at least the free wall section being flexurally elastic and operable for being deformed to deform the heart chamber free wall;
   the free wall section further being resiliently biased to automatically recoil after deformation to assist filling of the heart chamber.

2. The device of claim 1 wherein the free wall section includes at least one opening therein for passage of tissue fluid.

3. The device of claim 1 wherein the flexural elasticity of the free wall section varies along the free wall section.

4. The device of claim 1 wherein the flexural elasticity of the free wall section is generally isotropic along the free wall section.

5. The device of claim 1 wherein the jacket free wall section includes a plurality of springs that are formed to be flexurally elastic.

6. The device of claim 5 wherein the springs are in the form of at least one of a ribbon, a leaf, a corrugated sheet, a coil, a bar, and a serpentine wire.

7. The device of claim 5 wherein the springs are formed of a metal.

8. The device of claim 7 wherein the metal is selected from the group including titanium, a nickel-titanium alloy and stainless steel.

9. The device of claim 5 wherein at least the free wall section of the jacket includes one of polymer fibers or elastomeric polymer coupled with the springs for providing flexural elasticity.

10. The device of claim 5 wherein the springs are clad in a polyester mesh impregnated with an elastomeric polymer.

11. The device of claim 1 wherein the springs are formed of a material from the group including glass fibers, carbon fibers or composites of same.

12. The device of claim 1 wherein at least the free wall section of the jacket includes one of polymer fibers or elastomeric polymer for providing flexural elasticity.

13. The device of claim 1 further comprising a surface tension indicator incorporated with the jacket, the surface tension indicator operable for indicating the tightness of sutures for attaching the jacket to the heart.

14. The device of claim 13 wherein the surface tension indicator includes stacked layers forming a portion of the jacket, the stacked layers providing a color indication when compressed together by the tightness of the sutures.

15. The device of claim 13 wherein the surface tension indicator includes stacked layers forming a portion of the jacket, the stacked layers providing a grid indication when compressed together by the tightness of the sutures.

16. The device of claim 13 wherein the surface tension indicator includes an elastic element and an index, the elastic element being operable for stretching with respect to the index to give an indication of tension on a suture attached to the elastic element.

17. The device of claim 1 wherein the sleeve comprises a tubular portion and a flared portion.

18. The device of claim 17 wherein the flared portion includes a plurality of layers with particles trapped therebetween for providing protection of the base of the great vessel from the jacket.

19. The device of claim 17 wherein the flared portion includes a plurality of layers with at least one of a liquid or a gel trapped therebetween for providing protection of the base of the great vessel from the jacket.

20. The device of claim 1 wherein the collar comprises a tubular portion and a shingle portion.

* * * * *